United States Patent
Ding

(10) Patent No.: US 7,232,573 B1
(45) Date of Patent: Jun. 19, 2007

(54) STENT COATINGS CONTAINING SELF-ASSEMBLED MONOLAYERS

(75) Inventor: Ni Ding, San Jose, CA (US)

(73) Assignee: Advanced Cardiovascular Systems, Inc., Santa Clara, CA (US)

( * ) Notice: Subject to any disclaimer, the term of this patent is extended or adjusted under 35 U.S.C. 154(b) by 357 days.

(21) Appl. No.: 10/255,911

(22) Filed: Sep. 26, 2002

(51) Int. Cl.
*A61F 2/00* (2006.01)

(52) U.S. Cl. .................................................. 424/423

(58) Field of Classification Search ............... 424/423, 424/78.03
See application file for complete search history.

(56) References Cited

U.S. PATENT DOCUMENTS

| | | | | |
|---|---|---|---|---|
| 3,892,721 | A | * | 7/1975 | Gustafson .................. 526/320 |
| 4,733,665 | A | | 3/1988 | Palmaz ....................... 128/343 |
| 4,800,882 | A | | 1/1989 | Gianturco .................. 128/343 |
| 4,886,062 | A | | 12/1989 | Wiktor ........................ 128/343 |
| 4,977,901 | A | | 12/1990 | Ofstead ...................... 128/772 |
| 5,112,457 | A | | 5/1992 | Marchant .................... 204/165 |
| 5,328,471 | A | | 7/1994 | Slepian ........................ 604/101 |
| 5,455,040 | A | | 10/1995 | Marchant .................... 424/426 |
| 5,464,650 | A | | 11/1995 | Berg et al. ................... 427/2.3 |
| 5,578,073 | A | | 11/1996 | Haimovich et al. ............ 623/1 |
| 5,605,696 | A | | 2/1997 | Eury et al. .................. 424/423 |
| 5,667,767 | A | | 9/1997 | Greff et al. ............... 424/9.411 |
| 5,670,558 | A | | 9/1997 | Onishi et al. ............... 523/112 |
| 5,700,286 | A | | 12/1997 | Tartaglia et al. ................ 623/1 |
| 5,716,981 | A | | 2/1998 | Hunter et al. ............... 514/449 |
| 5,824,049 | A | | 10/1998 | Ragheb et al. ................. 623/1 |
| 5,830,178 | A | | 11/1998 | Jones et al. .................... 604/49 |
| 5,837,313 | A | | 11/1998 | Ding et al. ................. 427/2.21 |
| 5,851,508 | A | | 12/1998 | Greff et al. ............... 424/9.411 |
| 5,858,746 | A | | 1/1999 | Hubbell et al. ............. 435/177 |
| 5,865,814 | A | | 2/1999 | Tuch ........................... 604/265 |
| 5,873,904 | A | | 2/1999 | Ragheb et al. ................. 623/1 |
| 5,971,954 | A | | 10/1999 | Conway et al. ............... 604/96 |
| 5,980,928 | A | | 11/1999 | Terry .......................... 424/427 |
| 5,980,972 | A | | 11/1999 | Ding ......................... 427/2.24 |
| 6,015,541 | A | | 1/2000 | Greff et al. ................. 424/1.25 |
| 6,042,875 | A | | 3/2000 | Ding et al. ................. 427/2.24 |
| 6,051,648 | A | | 4/2000 | Rhee et al. .................. 525/54.1 |
| 6,056,993 | A | | 5/2000 | Leidner et al. ............. 427/2.25 |
| 6,060,451 | A | | 5/2000 | DiMaio et al. ................ 514/13 |
| 6,080,488 | A | | 6/2000 | Hostettler et al. ........ 428/423.3 |
| 6,096,070 | A | | 8/2000 | Ragheb et al. .................. 623/1 |
| 6,099,562 | A | | 8/2000 | Ding et al. .................. 623/1.46 |
| 6,110,188 | A | | 8/2000 | Narciso, Jr. ................. 606/153 |
| 6,113,629 | A | | 9/2000 | Ken ............................. 623/1.1 |
| 6,120,536 | A | | 9/2000 | Ding et al. .................. 623/1.43 |
| 6,120,904 | A | | 9/2000 | Hostettler et al. ........ 428/423.3 |
| 6,121,027 | A | | 9/2000 | Clapper et al. .............. 435/180 |
| 6,129,761 | A | | 10/2000 | Hubbell ........................ 623/11 |
| 6,153,252 | A | | 11/2000 | Hossainy et al. ............. 427/2.3 |
| 6,165,212 | A | | 12/2000 | Dereume et al. ........... 623/1.13 |
| 6,284,305 | B1 | * | 9/2001 | Ding et al. .................. 427/2.28 |
| 6,444,217 | B1 | * | 9/2002 | Kwok et al. .................. 424/423 |
| 6,444,219 | B2 | | 9/2002 | Rines et al. .................. 424/443 |
| 6,444,318 | B1 | * | 9/2002 | Guire et al. .................. 428/412 |
| 6,540,776 | B2 | * | 4/2003 | Sanders Millare et al. 623/1.15 |
| 2001/0014717 | A1 | * | 8/2001 | Hossainy et al. | |
| 2003/0004141 | A1 | * | 1/2003 | Brown ......................... 514/152 |

FOREIGN PATENT DOCUMENTS

| | | | |
|---|---|---|---|
| EP | 0 665 023 | | 8/1995 |
| EP | 0 970 711 | | 1/2000 |
| GB | 1601087 | * | 5/1978 |
| WO | WO 00/12147 | | 3/2000 |
| WO | WO 00/64506 | | 11/2000 |
| WO | WO 01/01890 | | 1/2001 |

OTHER PUBLICATIONS

Kwok et al., "Surface Modification of Polymers with Self-Assembled Molecular Structures: Multitechnique Surface Characterization," BioMacromolecules, Vol. 1, No. 1, pp. 139-148.*

* cited by examiner

*Primary Examiner*—Sharon E. Kennedy
(74) *Attorney, Agent, or Firm*—Squire, Sanders & Dempsey L.L.P.

(57) ABSTRACT

A coating for a medical device, particularly for a drug eluting stent, is described. The coating includes a self-assembled monolayer.

12 Claims, No Drawings

STENT COATINGS CONTAINING SELF-ASSEMBLED MONOLAYERS

BACKGROUND

1. Field of the Invention

This invention is directed to coatings for implantable medical devices, such as drug eluting vascular stents.

2. Description of the State of the Related Art

Percutaneous transluminal coronary angioplasty (PTCA) is a procedure for treating heart disease. A catheter assembly having a balloon portion is introduced percutaneously into the cardiovascular system of a patient via the brachial or femoral artery. The catheter assembly is advanced through the coronary vasculature until the balloon portion is positioned across the occlusive lesion. Once in position across the lesion, the balloon is inflated to a predetermined size to radially compress against the atherosclerotic plaque of the lesion to remodel the lumen wall. The balloon is then deflated to a smaller profile to allow the catheter to be withdrawn from the patient's vasculature.

A problem associated with the above procedure includes formation of intimal flaps or torn arterial linings which can collapse and occlude the conduit after the balloon is deflated. Moreover, thrombosis and restenosis of the artery may develop over several months after the procedure, which may require another angioplasty procedure or a surgical by-pass operation. To reduce the partial or total occlusion of the artery by the collapse of arterial lining and to reduce the chance of the development of thrombosis and restenosis, a stent is implanted in the lumen to maintain the vascular patency.

Stents are used not only as a mechanical intervention but also as a vehicle for providing biological therapy. As a mechanical intervention, stents act as scaffoldings, functioning to physically hold open and, if desired, to expand the wall of the passageway. Typically, stents are capable of being compressed, so that they can be inserted through small vessels via catheters, and then expanded to a larger diameter once they are at the desired location. Examples in patent literature disclosing stents which have been applied in PTCA procedures include stents illustrated in U.S. Pat. No. 4,733,665 issued to Palmaz, U.S. Pat. No. 4,800,882 issued to Gianturco, and U.S. Pat. No. 4,886,062 issued to Wiktor.

Biological therapy can be achieved by medicating the stents. Medicated stents provide for the local administration of a therapeutic substance at the diseased site. In order to provide an efficacious concentration to the treated site, systemic administration of such medication often produces adverse or toxic side effects for the patient. Local delivery is a preferred method of treatment in that smaller total levels of medication are administered in comparison to systemic dosages, but are concentrated at a specific site. Local delivery thus produces fewer side effects and achieves more favorable results. One proposed method for medicating stents involves the use of a polymeric carrier coated onto the surface of a stent. A solution which includes a solvent, a polymer dissolved in the solvent, and a therapeutic substance dispersed in the blend is applied to the stent. The solvent is allowed to evaporate, leaving on the stent surface a coating of the polymer and the therapeutic substance impregnated in the polymer.

To the extent that the mechanical functionality of stents has been optimized in recent years, it has been determined that continued improvements could be done by means of pharmacological therapies. For the purposes of pharmacological therapy, it is important to maintain the concentration of the drug at a therapeutically effective level for an acceptable period of time. Hence, controlling a rate of release of the drug from the stent is important.

In view of the foregoing, coatings for reducing the rate of release a therapeutic substance from implantable devices, such as stents, are desired. The coatings should prolong the residence time of the drug in the patient.

SUMMARY

According to one embodiment of the present invention, a coating for an implantable medical device is provided, the coating comprises a polymeric reservoir layer disposed on at least a portion of the device, and a self-assembled monolayer of molecules of an organic or elemento-organic substance disposed on the reservoir layer. The self-assembled monolayer can be chemically bonded to the reservoir layer. A therapeutic substance, for example, rapamycin, 40-O-(2-hydroxy)ethyl-rapamycin, 40-O-(3-hydroxy)propyl-rapamycin, 40-O-[2-(2-hydroxy)ethoxy]ethyl-rapamycin, or 40-O-tetrazole-rapamycin can be incorporated into the coating. An active agent, for example, polypeptide, heparin, hyaluronic acid, or superoxide dismutase mimics, can be optionally bonded to the self-assembled monolayer.

According to another embodiment of the present invention, a method for coating an implantable medical device is provided, the method comprises applying a polymeric reservoir layer on at least a portion of the device, and forming a self-assembled monolayer of molecules of an organic or elemento-organic substance on the reservoir layer.

DETAILED DESCRIPTION

A coating for an implantable medical device, such as a stent, can include a drug-polymer layer (also referred to as a "reservoir layer") or a drug layer free from any polymer, a topcoat layer, and a primer layer. The drug-polymer layer can serve as a reservoir for a therapeutically active agent or drug which is incorporated into the drug-polymer layer. The drug-polymer layer or the drug layer can be applied directly onto the stent surface. The topcoat layer can be applied over the reservoir layer or the drug layer. With the use of the drug layer free from any polymer, the use of a topcoat layer is needed.

The optional primer layer can be applied between the stent and the reservoir layer or the drug layer to improve the adhesion of the reservoir layer or the drug layer to the stent.

The topcoat layer, which can be essentially free from any therapeutic substances or drugs, serves as a rate limiting membrane which further controls the rate of release of the drug. By forcing the agent to diffuse through an additional coating layer prior to its release from the stent, the release of the active agent may be slowed.

The topcoat layer can be made of a self-assembled monolayer (SAM). For the purposes of this invention, SAM is defined as a thin film of an ordered monolayer of molecules of an organic or elemento-organic substance. The ordered film forms on the substrate surface when SAM molecules are attached to the substrate. The thickness of a SAM can be between about 10 and 40 Å.

Examples of suitable SAMs include substances having a general formula (I)

(I)

such as substances where A represents a methylene chain or a silicone-based chain.

SAM can be prepared by applying substance (I) on a stent having reservoir layer or a drug layer deposited over at least a portion of the stent. For the purposes of the present invention, substance (I) is referred to as a "SAM-forming substance." Any suitable SAM-fabrication technique known to those having ordinary skill in the art can be used. For example, a SAM-forming substance can be dissolved in an appropriate solvent, such as hexane. The solvent used to dissolve a SAM-forming substance should be incompatible with the drug and the polymer in the reservoir layer, so as to avoid extraction of the drug from the reservoir to the surface, and to avoid dissolving the polymer of the reservoir layer. The concentration of the SAM-forming substance in the solution can be typically between 0.01 mass % and 100 mass %. The stent can then be immersed into the solution, usually for a period of time which can be between a few minutes and several hours, for example, between about 1 hour and 72 hours, to allow the SAM-forming substance enough time to bond to the reservoir layer.

According to one embodiment of the present invention, methylene chain-based SAMs can be used to form the topcoat layer. For the methylene chain-based SAMs, "A" in formula (I) is the methylene group —$CH_2$—. Thus, the methylene chain-based SAM comprises a methylene chain having functional groups on one end or both ends of the chain. The structure of a substance forming a SAM can be represented by a general formula (II)

$$R—(CH_2)_n—R', \quad (II)$$

where the substitutents are the same (R=R') or different (R≠R'). Methylene chains can typically include between 10 and 50 carbon atoms (n=10–50). R and/or R' can usually include hydrogen, methyl, vinyl, anhydride, acyl chloride, hydroxyl, carboxyl, sulfonyl, acetate, trifluoro acetate, benzoate, isocyanate, epoxy, amino, thiol, succinimidal derivatives, or acrylic groups. At least one of R and R' can be a reactive group. For example, if R is methyl (a non-reactive group), R' will usually be a reactive group, e.g., hydroxyl, isocyanate or epoxy group.

SAM can be chemically bonded to the reservoir layer to form a topcoat layer. One way to bond the SAM is by forming covalent bonds between the SAM and the reservoir layer using the functionalities present in the SAM-forming substance and in the polymer forming the reservoir layer.

One example of a polymer having functional groups that can be used for bonding to a SAM is poly(ethylene-co-vinyl alcohol) having a general formula —[$CH_2$—$CH_2$]$_p$—[$CH_2$—$CH(OH)$]$_q$—. Poly(ethylene-co-vinyl alcohol) is known under the trade name EVAL and is manufactured by EVAL Company of America of Lisle, Ill., and can be obtained from Aldrich Chemical Co. of Milwaukee, Wis.

EVAL is a product of hydrolysis of ethylene-vinyl acetate copolymers. Those having ordinary skill in the art of polymer chemistry will understand that EVAL may also be a terpolymer and may include up to 5% (molar) units derived from styrene, propylene and other suitable unsaturated monomers. The hydroxyl functionality of EVAL can be used for chemical bonding to a SAM. Instead of EVAL, other polymers having hydroxyl groups can be utilized for preparing the reservoir layer. One example of such polymers is poly(methyl methacrylate-co-2-hydroxyethyl methacrylate) (PMMA-HEMA) having the formula

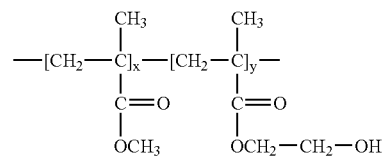

Other polymers having hydroxyl groups that can be used include poly(ethyl methacrylate-co-2-hydroxyethyl methacrylate) (PEMA-HEMA) and poly(butyl methacrylate-co-2-hydroxyethyl methacrylate) (PBMA-HEMA).

According to one embodiment, an isocyanate-terminated SAM-forming substance can be bonded to a polymer forming the reservoir layer containing hydroxyl groups. In the isocyanate-terminated SAM-forming substance, at least one of R and R' in formula (I) is the isocyanate group —N=C=O. Due to the presence of the isocyanate groups, isocyanate-terminated SAM-forming substance is chemically very active and readily reacts with EVAL. The isocyanate group, having strong electron accepting properties, reacts with nucleophilic hydroxyl group of EVAL, as illustrated by reaction scheme (III):

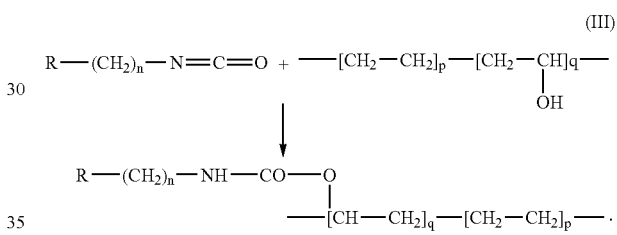

(III)

The conditions under which reaction (III) is conducted can be determined by those having ordinary skill in the art. Since the isocyanate group easily becomes inactive as a result of hydrolysis, reaction (III) is conducted in water- and moisture-free environment. If desired, EVAL can be replaced with another acceptable polymer containing hydroxyl groups. For example, isocyanate-terminated SAM-forming substance can be bonded to PMMA-HEMA utilizing hydroxyl groups of the HEMA component of PMMA-HEMA. As a result, SAM is firmly bonded to EVAL or another acceptable hydroxyl-containing polymer to form the urethane product of reaction (III).

According to another embodiment, an epoxy-terminated SAM-forming substance can be bonded to a polymer forming the reservoir layer containing hydroxyl groups. In the epoxy-terminated SAM-forming substance, at least one of R and R' in formulae (I) or (II) is the epoxy group

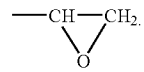

Epoxy groups in an epoxy-terminated SAM-forming substance are reactive, and can easily react with EVAL. The epoxy group can react with nucleophilic hydroxyl group of EVAL, via the nucleophilic substitution reaction $S_N2$. The ring opens and the epoxy-terminated SAM-forming substance is bonded to EVAL according to reaction scheme (IV):

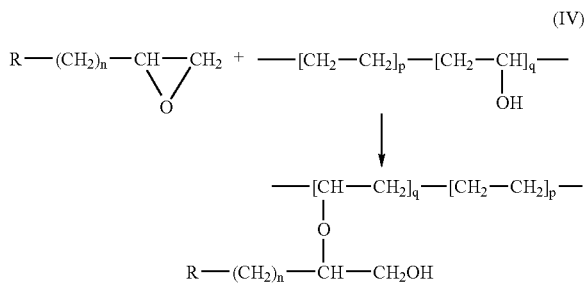

Reaction (IV) can be carried out more effectively in the presence of electron acceptors which facilitate electrophilic polarization of the C—O bond of the epoxy ring, thus making the subsequent attack by the proton of the hydroxyl group of EVAL easier. Accordingly, bonding of the epoxy-terminated SAM-forming substance to EVAL can be facilitated in the presence of electrophilic ring-opening catalysts, for instance, tertiary amines or aprotonic acids such as amine-boron trifluoride adducts. The use of any ring-opening catalyst is optional. The conditions under which this reaction is conducted can be determined by one having ordinary skill in the art. Again, other hydroxyl-containing polymers, such as PMMA-HEMA can be used instead of EVAL if desired.

According to another embodiment, an anhydride or acyl chloride group-terminated SAM-forming substance can be bonded to a polymer forming the reservoir layer containing hydroxyl groups. For example, in the anhydride-terminated SAM-forming substance, at least one of R and R' in formulae (I) or (II) is the anhydride group. Example of suitable anhydride-terminated and acyl chloride-terminated SAM-forming substances include lauric anhydride (also known as dodecanoic anhydride) having the formula $[CH_3—(CH_2)_{10}—CO]_2O$ and lauroyl chloride (also known as dodecanoyl chloride) having the formula $CH_3—(CH_2)_{10}—CO—Cl$. Anhydride or acyl chloride groups can react with hydroxyl groups of the reservoir layer. For example, in case of lauroyl chloride the reaction can be illustrated by reaction scheme (V):

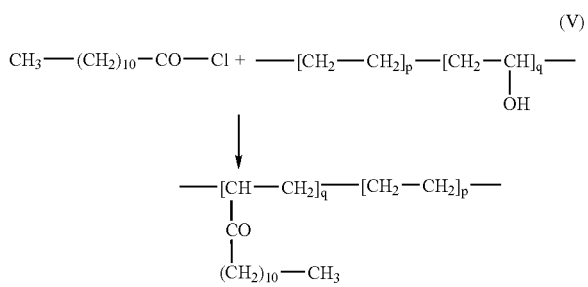

Reaction (V) is a typical reaction of esterification that can be accelerated by an acidic or basic catalyst, if desired.

According to yet another embodiment, an amino group-terminated SAM-forming substance can be bonded to a polymer forming the reservoir layer containing reactive groups such as hydroxyl groups or alternatively aldehyde or isocyanate groups. In the amino-terminated SAM-forming substance, at least one of R and R' in formulae (I) or (II) is the amino group —$NH_2$. Examples of a suitable amino-terminated SAM-forming substances include $C_{12}$–$C_{17}$ aliphatic amines, such as, laurylamine $C_{12}H_{24}NH_2$ available from Aldrich Chemical Company.

Amino-terminated SAM-forming substance can be conjugated to the hydroxyl-containing polymer forming the reservoir layer such as EVAL or PMMA-HEMA. To conjugate, as a first step EVAL can be preliminarily derivatized by tosylation (treatment with tosyl chloride), or alternatively by tresylation (by reacting with tresyl chloride). Tosyl chloride (TsCl) is a sulfonyl derivative of toluene, p-toluenesulfonyl chloride, having the formula $CH_3—C_6H_4—SO_2Cl$. Tresyl chloride or 2,2,2-trifluoroethanesulphonyl chloride (TrCl) is an aliphatic derivative of sulfonic acid having the formula $CF_3—CH_2—SO_2Cl$.

The process of EVAL derivatization can be conducted directly on the stent. In case of tosylation, the following process can be used. A 2% (mass) solution of EVAL in dimethylacetamide (DMAC) can be sprayed on the stent and dried for 10 minutes at 80° C., and then for 1 hour at 140° C. A 3% (mass) of TsCl in dry xylene can be prepared and the coated EVAL stent can be shaken for 1 minute with 1.4 ml of the TsCl solution. 0.25 ml of 33% (mass) of pyridine in dry xylene can be added, followed by shaking for 4 hours in a desiccator. The stent can be then rinsed with acetone and twice with 1 mM solution of HCl to remove the excess TsCl. As a result, EVAL can be tosylated according to reaction scheme (VI) and tosyl group is attached to the EVAL backbone via hydroxy group to yield the toluenesulfoester:

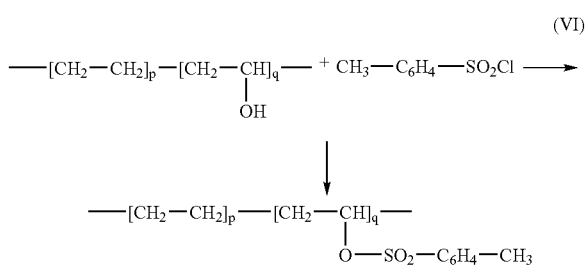

Alternatively, if tresylation is used to derivatrize EVAL, the process can be illustrated as shown by reaction scheme (VII) and as a result the tresyl group is attached to the EVAL backbone via hydroxy group:

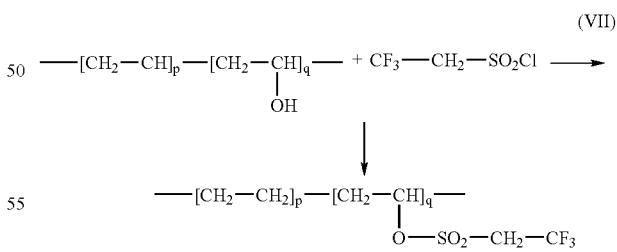

As a second step of conjugating, an amino-terminated SAM-forming substance is reacted with the derivatized EVAL. Since toluenesulfonic acid is known to be a very strong acid, on par with sulfuric or hydrochloric acids, its anion, $CH_3—C_6H_4—SO_3—$, is an excellent leaving group in the nucleophilic substitution alkylation reaction of a primary amine, much better than hydroxyl group of underivatized EVAL. Accordingly, the tosylated EVAL (the product of reaction (VI)) readily reacts with the amino-terminated SAM-forming substance as schematically shown by the alkylation reaction shown by reaction scheme (VIII):

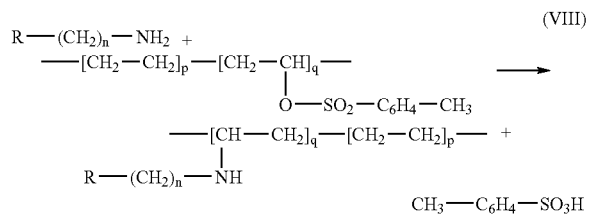
(VIII)

The conditions under which this reaction are conducted can be determined by those having ordinary skill in the art. The reaction of tresylated EVAL and the amino-terminated SAM-forming substance is similar to reaction (VIII). As a result, the amino-terminated SAM-forming substance is bonded to EVAL to form the secondary amine product of reaction (VIII).

Alternatively, other hydroxyl-containing polymers, such as PMMA-HEMA can be used instead of EVAL to bond the amino-terminated SAM-forming substance if desired. Those having ordinary skill in the art will appreciate that the chemistry of conjugating PMMA-HEMA or other suitable hydroxyl-containing polymers is similar to the processes described by reactions (V)–(VIII).

As another alternative, the alkylation of amines technique can be used to bond SAM-forming substance to the reservoir layer made of a polymer containing amino groups such as a poly(amino acid). In this case, the functions of the components are reversed—the SAM-forming substance provides the hydroxyl functionality and the reservoir polymer provides the amino functionality. The SAM-forming substance can be a hydroxyl-terminated compound, such as a long-chained aliphatic alcohol or diol. The chemistry of bonding the hydroxyl-terminated SAM-forming substance to an amino group-containing polymer of the reservoir layer is similar to the processes described by reactions (V)–(VIII).

Instead of the hydroxyl-terminated SAM-forming substance, a carboxyl-terminated SAM-forming substance can be used, for example a carbonic acid. In such a case, the carboxyl-terminated SAM-forming substance can be conjugated to the amino group-containing polymer of the reservoir layer to form an amide, under conditions to be determined by those having ordinary skill in the art.

If desired, the SAM-forming substance can be additionally modified. To modify, a biologically active reactive agent can be bonded to one terminus of the SAM-forming substance, while the functional group pendant on the other terminus can be used for bonding the SAM-forming substance to the polymer of the reservoir layer. Examples of biologically active reactive agents that can be bonded to the SAM-forming substance include polypeptides, heparin, hyaluronic acid, and oxidoreductases containing seven-coordinate complexes of manganese, also known as superoxide dismutase mimics (SODm).

Examples of suitable polypeptides include polymers and/or oligomers of L-arginine. L-arginine, also known as 2-amino-5-guanidinovaleric acid, is an amino acid having a formula $NH=C(NH_2)-NH-CH_2-CH_2-CH_2-CH(NH_2)-COOH$. Polymers and/or oligomers of L-arginine that can be used comprise a plurality of repeating monomeric amino acid units connected with peptide bonds, with a general formula $H[NH-CHX-CO]_p-OH$, where "p" can be within a range of 5 and 1,000, typically, within a range of between 6 and 20, and X is 1-guanidinopropyl radical having the chemical structure $-CH_2-CH_2-CH_2-NH-C(NH_2)=NH$. For example, a heptamer (designated R7), having p=7, can be used.

One example of bonding of a biologically active reactive agent is by using R7 and an amino group-terminated SAM-forming substance, for example a diamine having the formula $NH_2-(CH_2)_n-NH_2$. Grafting R7 to the amino group-terminated SAM-forming substance can be accomplished according to the following procedure. First, the non-protonated, non-terminal primary amino groups of R7 are protected by reaction with 9-fluorenylmethyl chloroformate in aqueous dioxane as shown by reaction scheme (IX). 9-fluorenylmethyl chloroformate also known as 9-fluorenylmethyloxycarbonylchloride or FMOC-chloride, has the formula

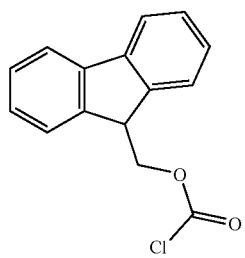

and is designated below as Q—O—C(O)—Cl.

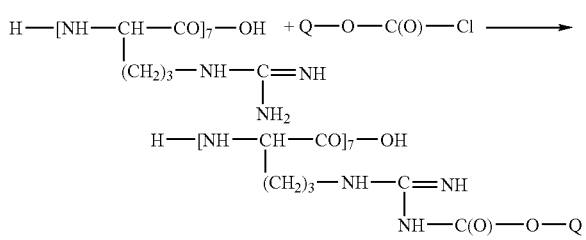
(IX)

where Q is 9-fluoreneylmethyl group. Alternatively, the amino groups of R7 can be protected using tert-BOC (di-tert-butyl dicarbonate) instead of FMOC-chloride.

Next, the protected R7 is reacted with an amino group-terminated SAM-forming substance to form amide derivatives. One example of a possible path of such reaction can be illustrated by reaction scheme (X), which can be carried in the presence of the equimolar or greater amount of 1-ethyl-3(3-dimethylaminopropyl) carbodiimide, also known as carbodiimide or EDC, having the formula $CH_3-CH_2-N=C=N-CH_2-CH_2-CH_2-N(CH_3)_2$. EDC is manufactured by Pierce Corp. of Rockford, Ill.

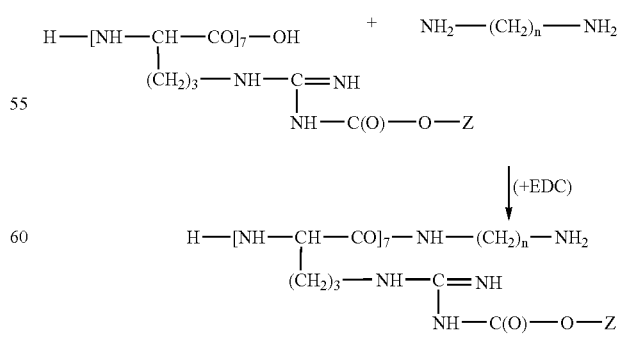
(X)

Finally, the product of reaction (X) can be cleaved by 50% morpholine or other appropriate amine. As a result, the 9-fluoreneylmethyl group is removed and R7 is tethered to the SAM-forming substance by the amide bond, as shown by the formula (XI):

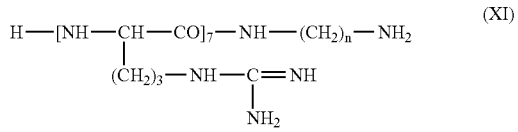

(XI)

Alternatively, the protected R7 can be conjugated to the SAM-forming substance by the reaction of direct esterification, which can be carried in the presence of 1,3-dicyclohexylcarbodiimide or dimethylamino pyridine. Regardless of which method of conjugation is selected, the final product (XI) is the same. The reactions described above are conducted under the standard conditions known to those having ordinary skill in the art.

The SAM-forming substance having R7 conjugated to it can then be bonded to the hydroxyl-containing polymer forming the reservoir layer according to the procedure described by reactions (V)–(VIII). As a result, the stent coating includes the SAM bonded to the polymer of the reservoir layer and R7 bonded to the SAM. Those having ordinary skill in the art will incorporate heparin, hyaluronic acid and other biologically active reactive agents into the stent coating using similar procedures, taking into account their chemical structures and choosing an appropriate synthesis accordingly.

The above-described embodiments discuss reservoir layers made of polymers that include a reactive group, such as hydroxyl, amino, or isocyanate group. Polymers not having the reactive groups can be pre-treated to generate the reactive groups so as to enable the bonding of the SAM-forming substance to the polymer of the reservoir layer.

For example, hydroxyl groups can be generated on the surface of a reservoir layer not originally containing hydroxyl groups by partially oxidizing the polymer forming the reservoir layer. The partial oxidation can be accomplished using low energy surface treatments known to those having ordinary skill in the art. The examples of such treatments include oxidative gas plasma treatment, corona discharge and electron beam treatment, oxidative gas treatments using, for example, ozone or a mixture of fluorine and oxygen, and chemical etching treatments using, for example, nitric acid or chromic acid.

In another embodiment, amino groups can be introduced on the surface of a reservoir layer not originally containing amino groups. For example, the surface of the reservoir polymer can be treated with ammonium and hydrogen gas plasma to generate amino groups. Alternatively, the surface of the reservoir polymer can be treated by oxygen plasma to generate aldehyde or ketone groups on the surface. The aldehyde or ketone groups can react directly with an amine-terminated SAM-forming substance to form a Schiff base, which can be optionally reduced to a secondary amine. Another alternative can be to react the aldehyde or ketone groups with hydroxylamine $H_2NOH$ followed by reduction to yield amino groups on the surface of the reservoir polymer.

The polymers not having reactive groups can be also used to make the reservoir layer. For instance, the SAM can be incorporated into the stent coating using UV-radiation curing techniques, for example by using the acrylate- or vinyl-terminated SAM-forming substance, described by formulae (I) or (II), where at least one of R and R' in formula (I) is the acrylic group or the vinyl group. Examples of suitable acrylate-terminated SAM-forming substances include lauryl acrylate (also known as dodecyl acrylate) having the formula $CH_2=CH-COO-(CH_2)_{11}-CH_3$ and lauryl methacrylate (also known as dodecyl methacrylate) having the formula $CH_2=C(CH_3)-COO-(CH_2)_{11}-CH_3$. One example of a suitable vinyl-terminated SAM-forming substance is vinyl decanoate having the formula $CH_3-(CH_2)_8-COO-CH=CH_2$.

The acrylate- or vinyl-terminated SAM-forming substance can be polymerized on the surface of the reservoir layer, for example, by UV-polymerization in the presence of a suitable photoinitiator such as benzophenone. The reservoir layer in this embodiment need not have functional groups as long as it has extractable hydrogen. The conditions under which the reaction of UV-polymerization is conducted can be determined by those having ordinary skill in the art.

The polymer of the reservoir layer can be any polymer otherwise suitable for making coatings for implantable medical devices such as stents. In addition to EVAL, PMMA-HEMA, PEMA-HEMA, PBMA-HEMA and poly (amino acids) discussed above, representative examples of polymers that can be used to fabricate the reservoir layer include poly(hydroxyvalerate), poly(L-lactic acid), polycaprolactone, poly(lactide-co-glycolide), poly(hydroxybutyrate), poly(hydroxybutyrate-co-valerate), polydioxanone, polyorthoester, polyanhydride, poly(glycolic acid), poly(D, L-lactic acid), poly(glycolic acid-co-trimethylene carbonate), polyphosphoester, polyphosphoester urethane, cyanoacrylates, poly(trimethylene carbonate), poly(iminocarbonate), co-poly(ether-esters) (e.g. PEO/PLA), poly-alkylene oxalates, polyphosphazenes, biomolecules (such as fibrin, fibrinogen, cellulose, starch, collagen and hyaluronic acid), polyurethanes (such as BIONATE available from Polymer Technology Group of Berkeley, Calif., or ELASTEON available from AorTech Biomaterials Co. of Chatswood, Australia), silicones, polyesters, polyolefins, polyisobutylene and ethylene-alphaolefin copolymers, acrylic polymers and copolymers (such as poly(butyl methacrylate), poly(ethyl methacrylate) or poly(hydroxyethyl methacrylate)), vinyl halide polymers and copolymers (such as polyvinyl chloride), polyvinyl ethers other than polyacetals, polyvinylidene halides (such as polyvinylidene fluoride and polyvinylidene chloride), polyacrylonitrile, polyvinyl ketones, polyvinyl aromatics (such as polystyrene), polyvinyl esters (such as polyvinyl acetate, acrylonitrile-styrene copolymers, ABS resins, and ethylene-vinyl acetate copolymers), polyamides (such as Nylon 66 and polycaprolactam), alkyd resins, polycarbonates, polyoxymethylenes, polyimides, polyethers, epoxy resins, polyurethanes, rayon, rayon-triacetate, cellulose, cellulose acetate, cellulose butyrate, cellulose acetate butyrate, cellophane, cellulose nitrate, cellulose propionate, cellulose ethers, and carboxymethyl cellulose. The selected polymer can have reactive groups. The presence of the reactive groups is however optional.

The drug-containing reservoir layer can be formed on the stent in any suitable manner. For example, a coating composition including a solvent, a polymer, and the drug can be applied to the stent by immersing the stent in the coating composition or by spraying the coating composition onto the stent. Following evaporation of the solvent, a reservoir layer of the polymer and the drug incorporated in the polymer is formed on the stent.

Alternatively, a polymeric reservoir layer, free from drugs, can be formed on the stent by any suitable method. The drug can then be introduced into the reservoir layer, for example, by placing the coated stent into a reaction flask containing the drug, allowing the agent to diffuse across the concentration gradient into the reservoir layer, and drying the stent to form a drug-containing reservoir layer on the stent.

The drug can include any substance capable of exerting a therapeutic or prophylactic effect for a patient. The drug may include small molecule drugs, peptides, proteins, oligonucleotides, and the like. The drug could be designed, for example, to inhibit the activity of vascular smooth muscle cells. It can be directed at inhibiting abnormal or inappropriate migration and/or proliferation of smooth muscle cells to inhibit restenosis.

Examples of drugs include antiproliferative substances such as actinomycin D, or derivatives and analogs thereof (manufactured by Sigma-Aldrich of Milwaukee, Wis., or COSMEGEN available from Merck). Synonyms of actinomycin D include dactinomycin, actinomycin IV, actinomycin $I_1$, actinomycin $X_1$, and actinomycin $C_1$. The active agent can also fall under the genus of antineoplastic, antiinflammatory, antiplatelet, anticoagulant, antifibrin, antithrombin, antimitotic, antibiotic, antiallergic and antioxidant substances. Examples of such antineoplastics and/or antimitotics include paclitaxel (e.g. TAXOL® by Bristol-Myers Squibb Co., Stamford, Conn.), docetaxel (e.g. Taxotere®, from Aventis S.A., Frankfurt, Germany) methotrexate, azathioprine, vincristine, vinblastine, fluorouracil, doxorubicin hydrochloride (e.g. Adriamycin® from Pharmacia & Upjohn, Peapack N.J.), and mitomycin (e.g. Mutamycin® from Bristol-Myers Squibb). Examples of such antiplatelets, anticoagulants, antifibrin, and antithrombins include sodium heparin, low molecular weight heparins, heparinoids, hirudin, argatroban, forskolin, vapiprost, prostacyclin and prostacyclin analogues, dextran, D-phe-pro-arg-chloromethylketone (synthetic antithrombin), dipyridamole, glycoprotein IIb/IIIa platelet membrane receptor antagonist antibody, recombinant hirudin, and thrombin inhibitors such as Angiomax™ (Biogen, Inc., Cambridge, Mass.). Examples of such cytostatic or antiproliferative agents include angiopeptin, angiotensin converting enzyme inhibitors such as captopril (e.g. Capoten® and Capozide® from Bristol-Myers Squibb Co., Stamford, Conn.), cilazapril or lisinopril (e.g. Prinivil® and Prinzide® from Merck & Co., Inc., Whitehouse Station, N.J.); calcium channel blockers (such as nifedipine), colchicine, fibroblast growth factor (FGF) antagonists, fish oil (omega 3-fatty acid), histamine antagonists, lovastatin (an inhibitor of HMG-CoA reductase, a cholesterol lowering drug, brand name Mevacor® from Merck & Co., Inc., Whitehouse Station, N.J.), monoclonal antibodies (such as those specific for Platelet-Derived Growth Factor (PDGF) receptors), nitroprusside, phosphodiesterase inhibitors, prostaglandin inhibitors, suramin, serotonin blockers, steroids, thioprotease inhibitors, triazolopyrimidine (a PDGF antagonist), and nitric oxide. An example of an antiallergic agent is permirolast potassium. Other therapeutic substances or agents which may be appropriate include alpha-interferon, genetically engineered epithelial cells, tacrolimus, dexamethasone, and rapamycin and structural derivatives or functional analogs thereof, such as 40-O-(2-hydroxy)ethyl-rapamycin (known by the trade name of EVEROLIMUS available from Novartis), 40-O-(3-hydroxy)propyl-rapamycin, 40-O-[2-(2-hydroxy)ethoxy]ethyl-rapamycin, and 40-O-tetrazole-rapamycin.

The coating of the present invention has been described in conjunction with a stent. However, the coating can also be used with a variety of other medical devices. Examples of the implantable medical device that can be used in conjunction with the embodiments of this invention include stent-grafts, grafts (e.g., aortic grafts), artificial heart valves, cerebrospinal fluid shunts, pacemaker electrodes, coronary shunts and endocardial leads (e.g., FINELINE and ENDOTAK, available from Guidant Corporation). The underlying structure of the device can be of virtually any design. The device can be made of a metallic material or an alloy such as, but not limited to, cobalt-chromium alloys (e.g., ELGILOY), stainless steel (316L), "MP35N," "MP20N," ELASTINITE (Nitinol), tantalum, tantalum-based alloys, nickel-titanium alloy, platinum, platinum-based alloys such as, e.g., platinum-iridium alloy, iridium, gold, magnesium, titanium, titanium-based alloys, zirconium-based alloys, or combinations thereof. Devices made from bioabsorbable or biostable polymers can also be used with the embodiments of the present invention.

EXAMPLES

Some embodiments of the present invention are further illustrated by the following example.

Example 1

A first composition can be prepared by mixing the following components:

(a) about 0.4 g of PBMA-HEMA, having a number average molecular weight of about 207,000 and a weight average molecular weight of about 378,000, with the molar ratio between the butylmethacrylate-derived units and the hydroxyethyl methacrylate-derived units of about 3:1;

(b) about 11.568 g of acetone;

(c) about 7.712 g of xylene; and (d) about 0.32 g of EVEROLIMUS.

The first composition can be applied onto the surface of a 13 mm TETRA stent (available from Guidant Corp.) by spraying and dried to form a drug-polymer layer. A spray coater having an EFD 7803 spray valve with 0.014 inch fan nozzle with a VALVEMATE 7040 control system, manufactured by EFD, Inc. of East Providence, R.I. can be used. The feed pressure can be about 0.2 atm (about 3 psi) and an atomization pressure can be about 1.35 atm (about 20 psi). The drug-polymer layer can be baked at about 80° C. for about one hour.

The drug-polymer layer-coated stent can be immersed into about 1 g of lauroyl chloride for about 1 hour, maintaining the temperature at about 50° C., under a nitrogen blanket to avoid moisture. The stent can then be removed, rinsed in cyclohexane to wash off the excess of lauroyl chloride, and dries at room temperature.

While particular embodiments of the present invention have been shown and described, it will be obvious to those skilled in the art that changes and modifications can be made without departing from this invention in its broader aspects. Therefore, the appended claims are to encompass within their scope all such changes and modifications as fall within the true spirit and scope of this invention.

What is claimed is:

1. A coating on an implantable medical device, the coating comprising a polymeric layer on at least a portion of the device, and a self-assembled monolayer of molecules of an organic or elemento-organic substance on the polymeric layer, wherein the polymeric layer consists of a polymer selected from the group consisting of poly(ethylene-co-vinyl alcohol) (EVAL), poly(methyl methacrylate-co-2-hydroxyethyl methacrylate) (PMMA-HEMA), poly(ethyl methacrylate-co-2-hydroxyethyl methacrylate) (PEMA-HEMA), and poly(butyl methacrylate-co-2-hydroxyethyl methacrylate) (PBMA-HEMA), and wherein the self-assembled monolayer has a thickness from about 10 Å to 40 Å.

2. The coating of claim 1, wherein the device is a stent.

3. The coating of claim 1, wherein the self-assembled monolayer is chemically bonded to the polymeric layer.

4. The coating of claim 1, further comprising a therapeutic substance incorporated in the coating.

5. The coating of claim 4, wherein the therapeutic substance is rapamycin, 40-O-(2-hydroxy)ethyl-rapamycin, 40-O-(3-hydroxy)propyl-rapamycin, 40-O-[2-(2-hydroxy)ethoxy]ethyl-rapamycin, or 40-O-tetrazole-rapamycin.

6. The coating of claim 1, wherein the self-assembled monolayer is prepared out of a substance having a methylene-based chain or a silicone-based chain.

7. The coating of claim 6, wherein the substance further includes at least one reactive substituent.

8. The coating of claim 7, wherein the reactive substituent is selected from a group consisting of hydroxyl, carboxyl, vinyl, anhydride, acyl chloride, sulfonyl, isocyanate, epoxy, amino, thiol, and acrylic.

9. The coating of claim 1, further comprising a biocompatible agent chemically bonded to the self-assembled monolayer.

10. The coating of claim 9, wherein the biocompatible agent is selected from a group consisting of polypeptides, heparin, hyaluronic acid, and superoxide dismutase mimics.

11. The coating of claim 1, wherein the polymer of the polymeric layer includes at least one reactive substituent.

12. The coating of claim 11, wherein the reactive substituent is selected from a group consisting of hydroxyl, amino, aldehyde, and isocyanate.

* * * * *